United States Patent [19]

Barlow et al.

[11] Patent Number: 5,456,259
[45] Date of Patent: Oct. 10, 1995

[54] ULTRASONIC TRANSDUCER ARRANGEMENT AND CATHETER

[75] Inventors: Christopher J. Barlow; Patrick J. Ryan; Robert J. Dickinson, all of London; Elvin L. Nix, Berkshire, all of United Kingdom

[73] Assignee: Intravascular Research Limited, London, United Kingdom

[21] Appl. No.: 190,066

[22] PCT Filed: Jul. 30, 1992

[86] PCT No.: PCT/GB92/01412

§ 371 Date: Jan. 31, 1994

§ 102(e) Date: Jan. 31, 1994

[87] PCT Pub. No.: WO/0002809

PCT Pub. Date: Feb. 18, 1993

[30] Foreign Application Priority Data

Jul. 30, 1991 [GB] United Kingdom ............... 9116478

[51] Int. Cl.⁶ .................................................. A61B 8/12
[52] U.S. Cl. .............................. 128/662.03; 128/662.06
[58] Field of Search ............... 606/159; 128/660.01, 128/660.03, 661.01, 662.03, 662.06; 73/626

[56] References Cited

U.S. PATENT DOCUMENTS

| | | | |
|---|---|---|---|
| 3,827,115 | 8/1974 | Bom | 128/662.06 |
| 3,938,502 | 2/1976 | Bom | 128/662.06 |
| 4,759,372 | 7/1988 | Umemura et al. | 128/661.01 |
| 4,841,977 | 6/1989 | Griffith et al. | 128/660.03 |
| 4,917,097 | 4/1990 | Proudion et al. | 128/662.06 |
| 5,027,659 | 7/1991 | Bele et al. | 128/661.01 X |
| 5,081,993 | 1/1992 | Kitney et al. | 128/662.06 X |
| 5,183,048 | 2/1993 | Eberle | 128/661.01 X |
| 5,186,177 | 2/1993 | O'Donnell et al. | 128/661.01 X |

FOREIGN PATENT DOCUMENTS

| | | |
|---|---|---|
| 0118329 | 10/1984 | European Pat. Off. . |
| 2163295 | 3/1986 | United Kingdom . |
| 2195821 | 4/1988 | United Kingdom . |
| 2208138 | 1/1989 | United Kingdom . |
| 2216751 | 10/1989 | United Kingdom . |
| 2246632 | 7/1992 | United Kingdom . |

OTHER PUBLICATIONS

Patent Abstracts of Japan, vol. 2, No. 7, (E–005), Jan. 18, 1978; and JP, 52–123265 (Oki Denki Kogyo K.K.), Oct. 17, 1977.

Patent Abstracts of Japan, vol. 4, No. 67, (E–11) (549), May 20, 1980; and JP, 55–35526 (Itsuki Ban), Mar. 12, 1980.

*Primary Examiner*—Francis Jaworski
*Attorney, Agent, or Firm*—Tarolli, Sundheim & Covell

[57] ABSTRACT

A catheter (1a, 1b) is provided with an ultrasonic transducer array at its tip (3), the transducer array having been manufactured from an annulus of piezoelectric material (10) by making longitudinal mutually parallel slots (18) in the material.

28 Claims, 9 Drawing Sheets

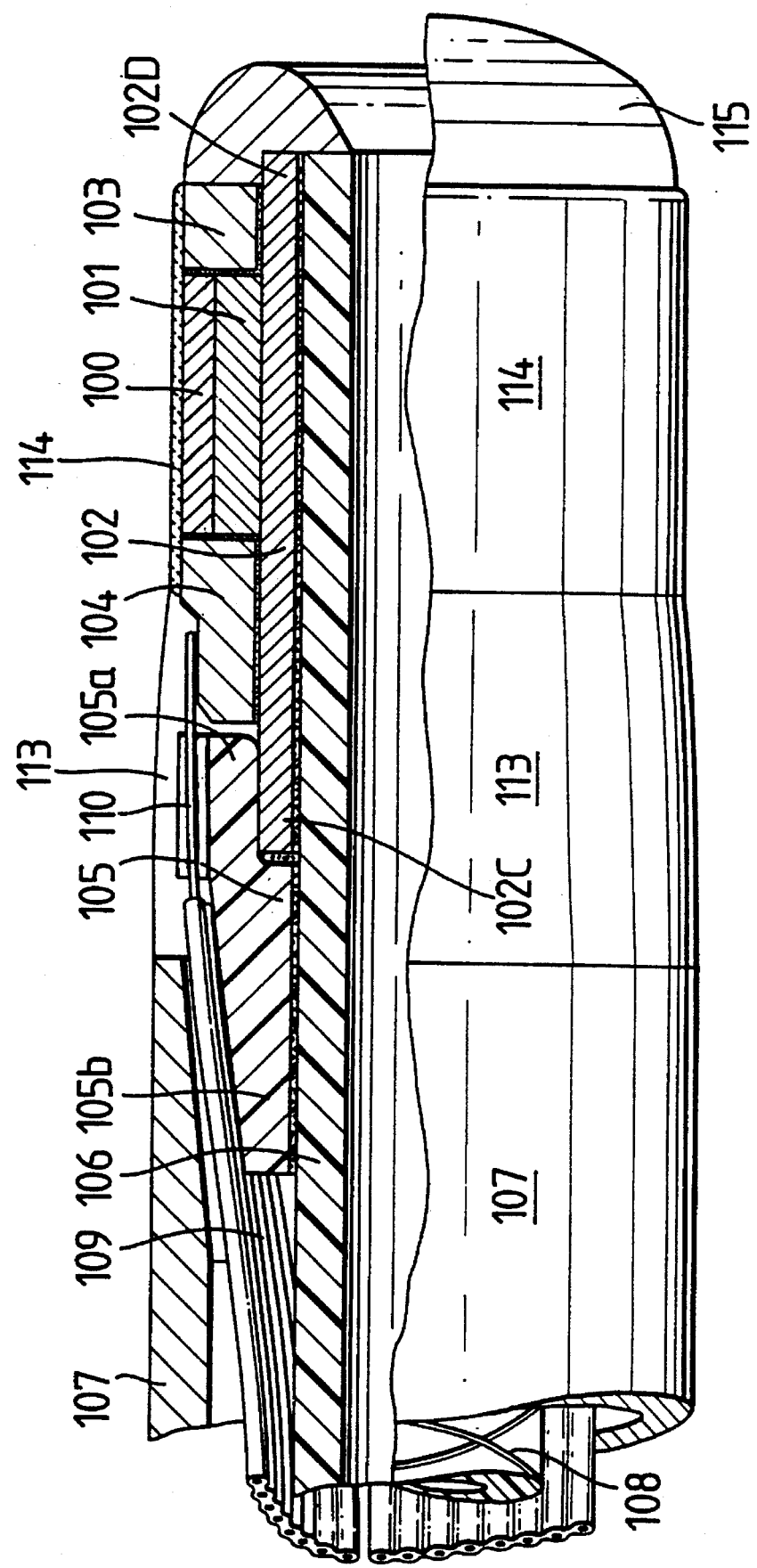

ULTRASONIC TRANSDUCER ARRANGEMENT AND CATHETER

FIELD OF THE INVENTION

The present invention relates to an ultrasonic transducer arrangement and catheter and more particularly to one for use in a system of the kind disclosed in our international patent application WO89/04142.

BACKGROUND OF THE INVENTION

In that patent application there is disclosed a system for visualising internal human organs by means of an invasive ultrasonic technique.

In that system ultrasonic signals are generated and received by a transducer assembly mounted on the distal end of a catheter to be inserted into the patient. The present invention is concerned with the construction and manufacture of such a transducer arrangement and catheter.

The transducer arrangement of that earlier patent application consists essentially of a cylindrical array of piezo-electric crystal transducer elements. In the embodiment described in that earlier patent application, there are twelve such elements. Each element is discrete and is mounted in a groove formed in the circumference of a core member.

As explained in that earlier patent application, the degree of visual resolution obtainable depends upon the rate of signal output and resultant echo signal. This rate can be increased by increasing the number of transducer elements or alternatively by rotating a given number of transducer elements, as indicated in that earlier patent application.

There are clearly advantages and disadvantages associated with either attempting to increase the number of transducer elements in the case of a stationary transducer (i.e non-rotatable) and attempts to provide a drive arrangement for a rotatable transducer arrangement having fewer elements.

These difficulties are due to the very small scale involved in this type of transducer arrangement. Typically, the catheter at the end of which the transducer arrangement is mounted is less than 2.0 mm in diameter and typically 1.0 mm. It can thus be appreciated that the extremely small size of the transducer arrangement as a whole imposes limitations on the number of transducer elements which can be accommodated around the circumference. Equally, because of the very small scale involved, it is difficult to provide a rotatable transducer arrangement with an appropriate drive arrangement that can operate through tortuous vessels.

The present invention is concerned with improving the visual resolution referred to earlier by increasing the number of transducer elements beyond the maximum number which it had up to the present time been thought practicable in such a small scale arrangement.

SUMMARY OF THE PRESENT INVENTION

According to a first aspect of the present invention, in a transducer arrangement of the kind described, the transducer elements are formed from a single annulus, each transducer element being defined in relation to adjacent transducer elements by a physical discontinuity between adjacent elements to render each element separate from the other elements and the arrangement is characterised in that the transducer array has a diameter no greater than two millimetres and typically one millimetre and a number of discrete transducer elements not less than thirty-two and preferably not less than forty-eight and even more preferably not less than sixty-four.

The physical discontinuity could take the form of a slot which has been formed in the annulus by means of a laser beam, a grinding or sawing operation, a chemical etching operation or combination of these.

According to a second aspect of the present invention, the transducer array is manufactured from a single annulus of electrically polarised lead zirconate titanate (PZT), the individual transducer elements being defined by circumferentially spaced slots which. run substantially parallel to the axis of the annulus. The PZT may be electrically polarised before or after creation of the slots.

According to a third aspect of the present invention, the PZT cylindrical annulus is mounted on a tungsten carbide tube or other suitable rigid conducting tube to which it is bonded.

According to a fourth aspect of the present invention, the steps involved in manufacturing the transducer array include the steps of bonding the cylindrical annulus of PZT to a support tube typically of tungsten carbide, then accurately lapping or machining the wall thickness of the PZT cylinder to the desired .wall thickness (typically 0.1 mm or less) and then forming the aforesaid slots in the PZT cylinder in order to define the individual transducer elements.

According to a fifth aspect of the present invention, the piezo-electric cylindrical annulus defining the transducer array has an axially extending portion or flange which is adapted to support electrical contact points for the electrical energisation of the transducer array and the return of echo signals from the transducer array.

According to a sixth aspect of the present invention, the accurate concentric location and bonding of the inner surface of the piezo-electric cylindrical member to the support member is achieved by forming either the said inner surface of the piezo-electric annulus or the outer surface of the support member, with indentations so that the indentations accommodate bonding material and the peaks of the walls defining the indentations abut the support member or piezo-electric annulus respectively to thus accurately locate the two members.

A preferred formation of the indentations comprises a screw thread or parallel circumferential grooves.

According to an seventh aspect of the-present invention, in a method of manufacturing the transducer arrangement the piezo-electric annulus has its internal diameter accurately formed by means of a tapered grinding element.

According to a eighth aspect of the present invention during the manufacture of the transducer arrangement the piezo-electric annulus and the support are held in accurate concentricity with respect to one another, there being an annular gap between the two members, adhesive then being introduced into the gap to bond the two members together.

According to a ninth aspect of the present invention, the piezo-electric annulus has adjacent to each of its axial ends a ceramic annulus, each of which serves to support the piezo-electric annulus during the slotting operation and grinding of the required profile. The PZT is only supported by the adhesive whereas the ceramic annuli are supported more directly on the tungsten carbide collar. The slots segment the PZT but not the ceramic annuli.

According to an tenth aspect of the present invention, electrical connections to the piezo-electric transducer array are effected by means of a metallised layer formed on the piezo-electric material by sputtering.

According to a eleventh aspect of the present invention, the electrically conducting tracks are formed on a flexible support which is then mounted on the piezo-electric annulus. The flexible support is preferably made from the material known as "Kapton" which is a form of polyamide. The electrically conductive tracks are defined by standard photolithographic and chemical etching techniques, in a thin Kapton sheet carrying a thin copper coating.

According to a twelfth aspect of the present invention, the "front" or radially outer face of the piezo-electric annulus is rendered both acoustically matching and biocompatible by an appropriate coating.

According to a thirteenth aspect of the present invention the piezo-electric cylindrical annulus defining the transducer array has an axially extending portion of smaller diameter than the external diameter of the annulus which smaller diameter portion is divided into separate axially extending bond pads to which individual electrical leads are secured respectively for the electrical energisation of the transducer array elements and the return of echo signals from the transducer array elements.

According to a fourteenth aspect of the present invention, the optimum aspect ratio for each transducer element for a given diameter of transducer annulus is achieved by electrically connecting more than one element to a single electrical conductor.

According to a fifteenth aspect of the present invention a resilient sleeve is provided having axially extending slots through which electrical conductors pass and are gripped thereby before making electrical contact with the transducer elements.

Accordeing to a sixteenth aspect of the present invention the ends of the electrical conductors are bonded to the bond pads.

According to an seventeenth aspect of the present invention the supply cables are in the form of ribbon cables having a pitch matched to the pitch of the bond pads in the transducer annulus and to the slot pitch in the resilient sleeve.

BRIEF DESCRIPTION OF THE DRAWINGS

How the invention may be carried out will now be described by way of example only and with reference to the accompanying drawings in which:

FIGS. 10 to 17 illustrate the various stages in the manufacture of a second and preferred embodiment of the present invention in which:

FIG. 10 is a perspective diagrammatic view of the first stage in the manufacturing process;

FIG. 11 is a view similar to FIG. 10 showing the second stage in the manufacturing process;

FIG. 12 is a view similar to FIG. 10 showing a third stage in the manufacturing process;

FIG. 13 is a view similar to FIG. 10 showing a fourth stage in the manufacturing process;

FIG. 14 is a partial cross-sectional view on the line B–B' of FIG. 13;

FIG. 15 is a part longitudinal section of the finished transducer arrangement;

FIG. 16 is a perspective diagrammatical view, partly in section, of the finished transducer arrangement; and FIG. 17 is a section taken on the line C–C' of FIG. 16.

FIG. 1

Figure 1:
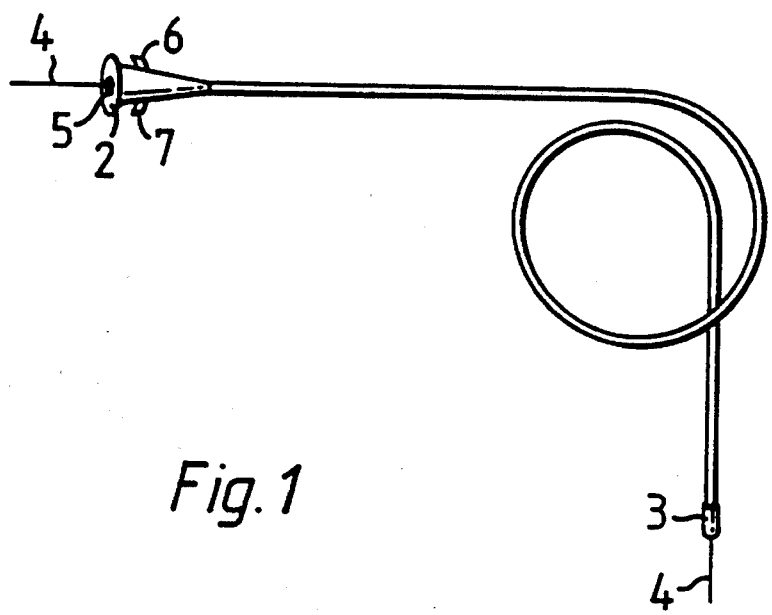
FIG. 1 shows a known type of catheter of the kind to which the present invention is applied.

This illustrates a typical known type of catheter which consists of a plastic tube 1 which has a handle 2 at the proximal end and a tip member 3 at the distal end. A guide wire 4 can be passed through the tube 1. The handle 2 is provided with an axially located aperture 5 through which the guide wire 4 can pass. The handle is also provided with further radially located apertures 6 and 7.

The distal end 3 of the catheter is adapted to be inserted into a patient, for example into a patient's artery, by use of the guide wire 4 in known manner.

The present invention is concerned with the mounting, construction and manufacture of an ultrasonic transducer element to be carried at the distal end 3 of the catheter.

A catheter of the kind shown in FIG. 1 can be of various diameters but in the case of a catheter for insertion into an artery, the outside diameter of the tube 1 would typically be not greater than 2.0 mm.

FIGS. 2 AND 3

In this embodiment of the invention, the catheter comprises an inner tube 1a and an outer tube 1b both of which are made from a suitable moulded plastics material, such as nylon.

An electrically conducting tubular support 8, manufactured from tungsten carbide, is carried on the outer circumferential surface of the inner catheter tube 1a there being a bond 9 between the inner tube 1a and the metal support tube 8. In this embodiment, the bond 9 consists of a silver loaded epoxy resin.

A piezo-electric transducer array in the form of a grooved annulus 10 is mounted on the outer circumferential surface of the support tube 8 by means of bonding 11 which again consists of a silver loaded epoxy resin.

The radially outer or "front-face" of the piezo-electric transducer annulus 10 is coated with a quarter-wave layer 12 of some suitable material such as a loaded epoxy resin or nylon. This quarter-wave layer 12 is conventional in piezo-electric transducers and its purpose is to improve the acoustic performance of the transducer and to shield the patient from any toxic effect of the piezo-electric material.

Figure 3:
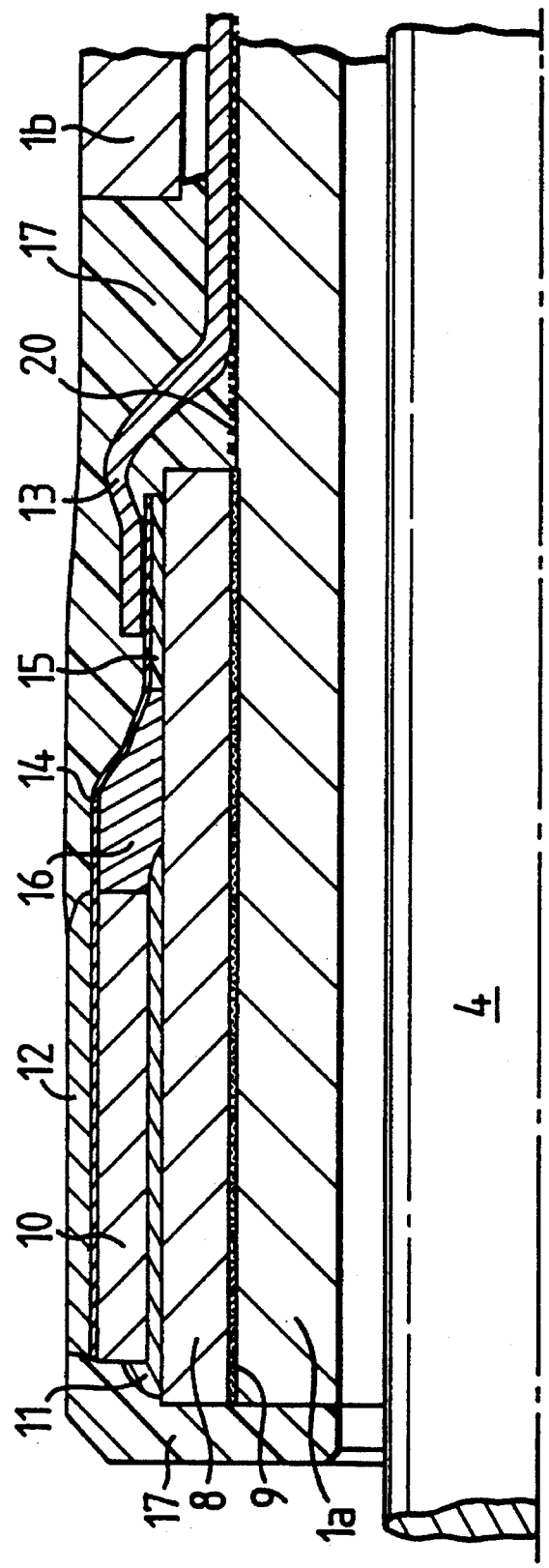
FIG. 3 is a half-sectional view taken on the line A–A$^1$ of FIG. 2 but including encapsulating material not shown in FIG. 2.

The segments of the piezo-electric annulus 10 are energised by electrical connections, one of which is shown in FIG. 3 at 13. The distal end 13a of the electrical connection 13 (which in this example is a ribbon cable) contacts a metallisation layer 14 which extends from the radially outer face of the piezo-electric annulus 10 to an alumina pad 15 carried by the axially inner end of the tungsten carbide tube 8.

There is an insulating epoxy bonding 16 between the pad 15 and the piezo-electric annulus 10.

The assembly just described is encased in a layer of polyurethane 17 in the manner indicated in FIG. 3. The radially outer surface of the "front-face" coating layer 12 is however exposed and not covered by the polyurethane 17. The metallisation layer 14 in this embodiment is formed of gold.

The piezo-electric annulus 10 has sixty-four radially equally spaced slots or grooves 18 running axially of the annulus and parallel to its axis and where depth extends down into the support 8 in order to define between each pair of adjacent slots 18 a discrete transducer segment or element 19 thus giving a total of sixty-four transducer segments or elements for the piezo-electric transducer as a whole.

Figure 2:
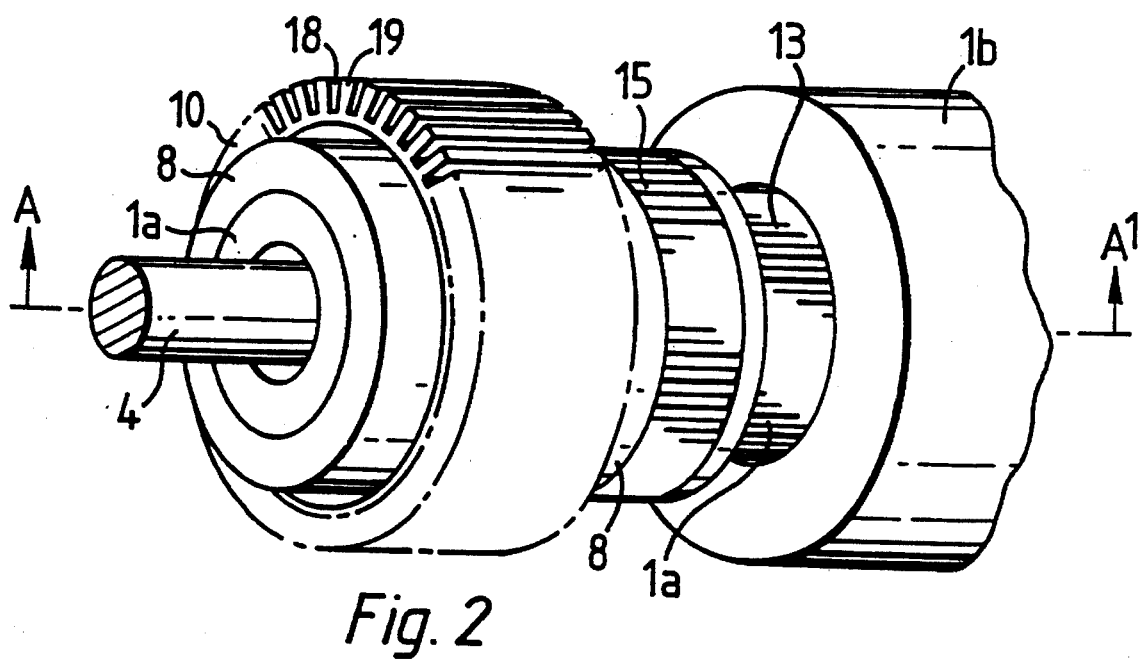
FIG. 2 is an enlarged fragmentary perspective view of a transducer arrangement according to the present invention, mounted on the distal end of a catheter of the kind shown in FIG. 1.

The method of manufacturing the transducer assembly described with reference to and as shown in FIGS. 2 and 3 will be described later.

As indicated earlier, the electrical energisation of the piezo-electric transducer elements 19 is effected by means of electrical connections such as 13 (FIG. 3). The earth return is via the silver loaded epoxy resin bonding 9 and an electrically conducting braid 20 mounted on the outside of the inner catheter tube 1a. This is shown more clearly in FIG. 4.

As an alternative to having the individual ribbon leads 13 shown in FIG. 3, axially extending electro-plated conductors 21 could be formed on an electrically insulating coating 22 to separate those conductors from the braid 20. These tracks could be formed by laser evaporation of a thin metallic layer and then electroplated to thicken them.

Method of Manufacture

Figure 4:
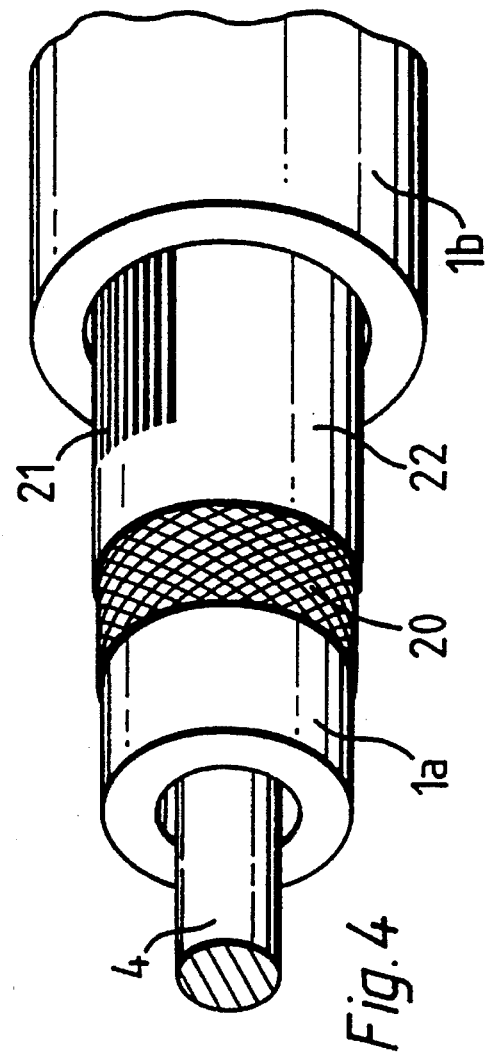
FIG. 4 is a view similar to FIG. 2 but showing an arrangement for making the electrical connections with the transducer array.

As indicated earlier in this specification, the assembly shown in FIGS. 2 to 4 is of extremely small dimensions. The overall diameter of the assembly shown in FIG. 3 is 1.1 mm. The inside diameter of the piezo-electric annulus 10 is about 0.90 mm and the outside diameter is about 1.06 mm. The inside and outside diameters respectively of the inner catheter tube 1a are about 0.50 mm and 0.65 mm respectively and the inner and outer diameters of the tungsten carbide support tube 8 are about 0.71 mm and 0.89 mm respectively.

It will be appreciated that with these extremely small dimensions the manufacture of the assembly illustrated in FIGS. 2 to 4 gives rise to problems which would not be critical in a structure having much larger dimensions. Thus, there are problems which are peculiar to the manufacture of a high resolution transducer assembly for mounting on the distal end of a very small diameter catheter.

One particular problem concerns the obtaining of accurate concentricity between the support tube 8 and the piezo-electric annulus 10. It is most important to maintain this concentricity during manufacture because otherwise some transducer elements 19 will be farther from the axis of the catheter than other transducer elements 19 thus giving rise to inaccuracies in the deductions which can be made from the echo signals received from the transducer assembly.

As indicated earlier, the piezo-electric annulus 10 is glued to the outer cylindrical surface of the metal support tube 8 by means of silver loaded epoxy resin 11 or by a soldered or brazed metallic layer.

In order to achieve accurate concentricity between these two elements 8 and 10, it is necessary to ensure that during the manufacturing operation, and in particular the provision of the adhesive 11 between the two elements 8 and 10, that the two elements do not "float" with respect to each other into a non-concentric relationship. The present invention is concerned with overcoming this problem and has arrived at a number of solutions.

Figure 5:
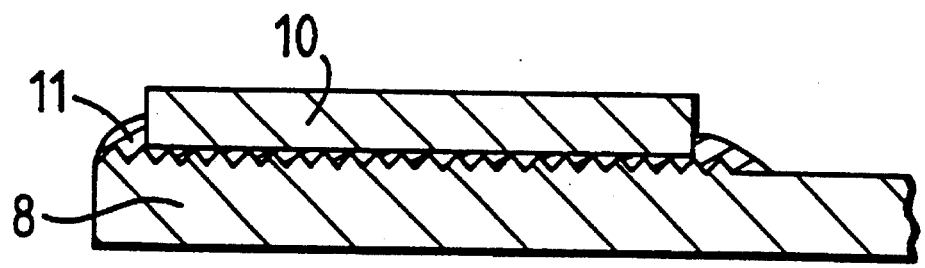
FIG. 5 shows a detailed fragmentary sectional view of the interface between the inner surface of the piezo-electric annulus and its support according to an alternative embodiment.

FIG. 5 illustrates one solution to this problem. In this embodiment either the circumferentially outer surface of the metal support tube 8 or the circumferentially inner surface of the piezo-electric annulus 10 is formed with protrusions and/or hollows so that only part of that surface is in contact with the other member, i.e the piezo-electric annulus 10 or the metal support tube 8 respectively. In the embodiment shown in FIG. 6, the circumferentially outer surface of the metal support tube 8 is formed with a thread 24, the adhesive 11 being contained within the thread. With this arrangement, the material forming the outer diameter of the thread contacts the circumferentially inner surface of the piezo-electric annulus 10 to thus locate it at the correct co-axial position in relation to the axis of the support tube 8. At the same time the helical recess formed by the thread accommodates the adhesive 11 which thereby has substantially the same surface area in contact with the piezo-electric annulus as would be the case if the circumferentially outer surface of the support tube 8 were cylindrical. The contact area between the adhesive 11 and the outer surface of the support tube 8 is substantially increased by virtue of the thread. Therefore, not only is concentricity ensured but adhesion between these two elements is improved.

Figure 6:
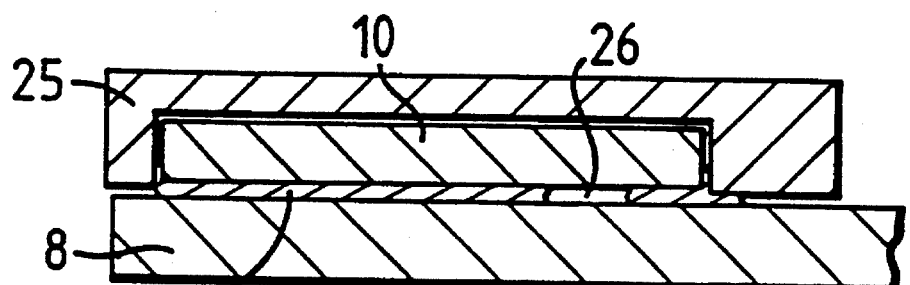
FIG. 6 is a view similar to FIG. 5 but showing a step in the manufacture of the transducer array using a sacrificial jig.

An alternative method of manufacture to ensure concentricity is illustrated in FIG. 6. In this method an aluminium "sacrificial" jig 25 is used to hold the piezo-electric annulus 10 accurately in relation to the supporting metal tube 8. There is a gap 26 between the piezo-electric annulus 10 and the metal tube 8 into which gap the adhesive 11 is sucked by having means for lowering the pressure in the gap at the right hand side of FIG. 6. After the adhesive 11 has set, thus bonding the piezo-electric annulus 10 to the supporting metal tube 8, the aluminium jig 25 is dissolved, by for example using sodium hydroxide.

Figure 7:
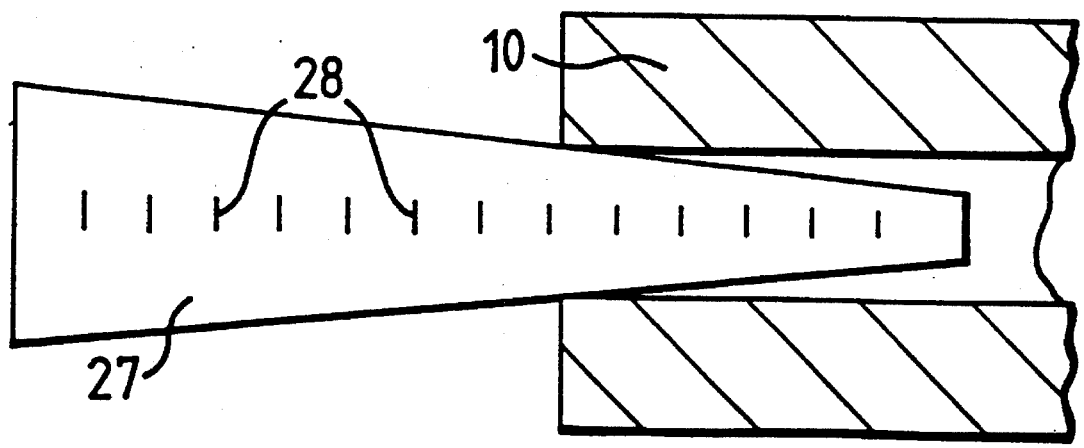
FIG. 7 is a view similar to FIG. 5 showing a method during manufacture, of accurately forming the internal diameter of the piezo-electric annulus.

Prior to the manufacturing step just described with reference to FIGS. 5 and 6, it is necessary to accurately form the piezo-electric annulus 10 with the required internal diameter. FIG. 7 illustrates diagramatically a preferred method of producing that desired internal diameter.

In FIG. 7 the piezo-electric annulus 10 is shown at the stage when it is, as it were, a "blank" which has not been turned to either the requisite internal diameter or the requisite external diameter.

The "blank" piezo-electric annulus 10 has an internal diameter significantly smaller than that eventually required for accurate mounting on the metal support tube 8.

A tapered mandrel 27, having axially spaced calibrations 28 is employed to grind away the circumferential inner surface of the piezo-electric annular blank 10. The mandrel 27 has an abrasive outer surface and is rotated, as indicated, and moved slowly axially to the right as viewed in FIG. 7 to progressively grind away the circumferentially inner surface of the piezo-electric annulus 10. This operation continues until the desired inner diameter of that annulus is achieved, as indicated by the appropriate axial position of the appropriate calibration 28 in relation to the left hand end face of the piezo-electric annulus 10 as viewed in FIG. 7. The mandrel has a length approximately one-hundred times greater than the axial length of the annular blank 10 and the gradient of the taper is approximately one-in-a-thousand. This enables the internal diameter of the annular blank 10 to be grooved to very accurate limits.

After the piezo-electric annulus 10 has been bonded to the metal support tube 8 the outside diameter of the annulus 10 is reduced to the desired external diameter by an appropriate operation such as grinding.

The axially extending circumferential slots or grooves 18 are then formed in the annulus 10 to define the individual transducer elements 19. This can be done in a number of ways including by means of laser ablation, laser assisted chemical etching or by a mechanical sawing operation. The latter is preferred because it is less susceptible to inaccuracies resulting in the finished slot or groove due to the inhomogeneous nature of the piezo-electric material.

As indicated earlier, because of the extremely small scale of the transducer assembly already described, any slight inaccuracies in manufacture become critical to the effective operation of the transducer. One source of such inaccuracies has been found to be caused by relative movement of the components of the assembly after complete assembly has been carried out, i.e there is a tendency for the components to move relative to one another even after the final encapsulation of the assembly in the aforementioned polyurethane coating 17.

Figure 8:
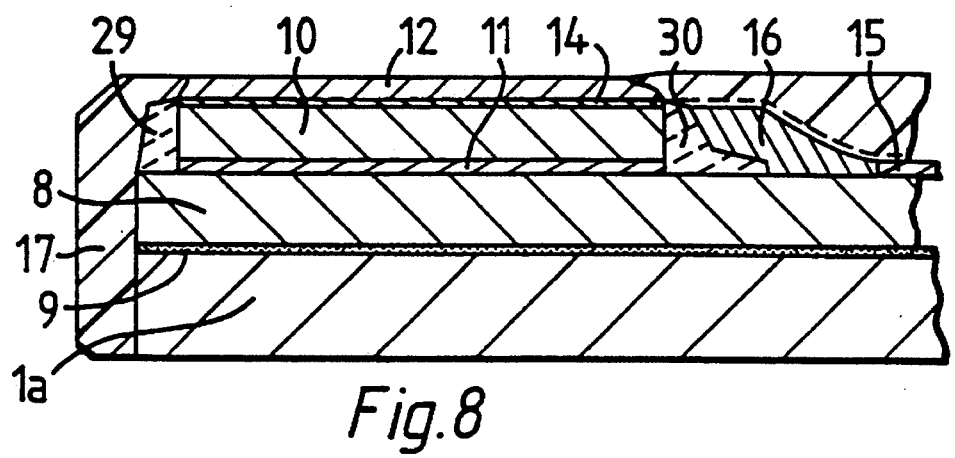
FIG. 8 is a view similar to FIG. 3 showing an alternative way of mounting the piezo-electric annulus on its support.

The present invention is therefore also concerned with increasing the stability of the final assembly. FIG. 8 illustrates a modification of the assembly which is aimed at increasing the stability of the assembly.

In the arrangement of FIGS. 2 and 3, the axial ends of the piezo-electric annulus 10 are contained in an axial direction by the epoxy bonding 16 at one end and the overflow of the silver loaded epoxy resin 11 at the other. To increase the stability of the final assembly, two ceramic rings 29 and 30 are employed in the embodiment of FIG. 8. The inner circumferential surfaces of these rings 29, 30 are bonded to the outer circumferential surface of the tungsten carbide support tube 8. The material from which the ceramic rings 29 and 30 are made is preferably alumina and the bonding is non-conducting and preferably an epoxy.

Figure 9:
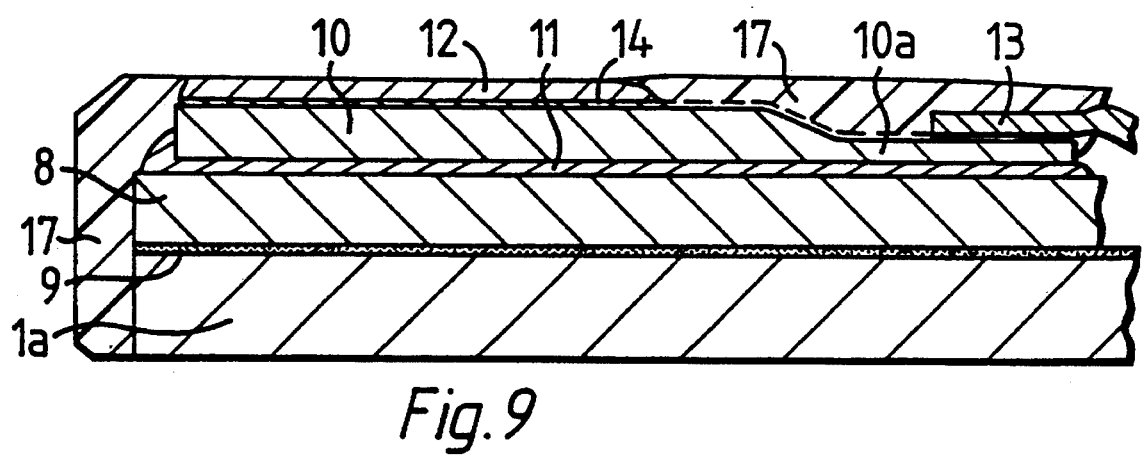
FIG. 9 is a view similar to FIG. 3 showing the piezo-electric annulus axially extended to form the pad for the electrical connection.
Figure 10:
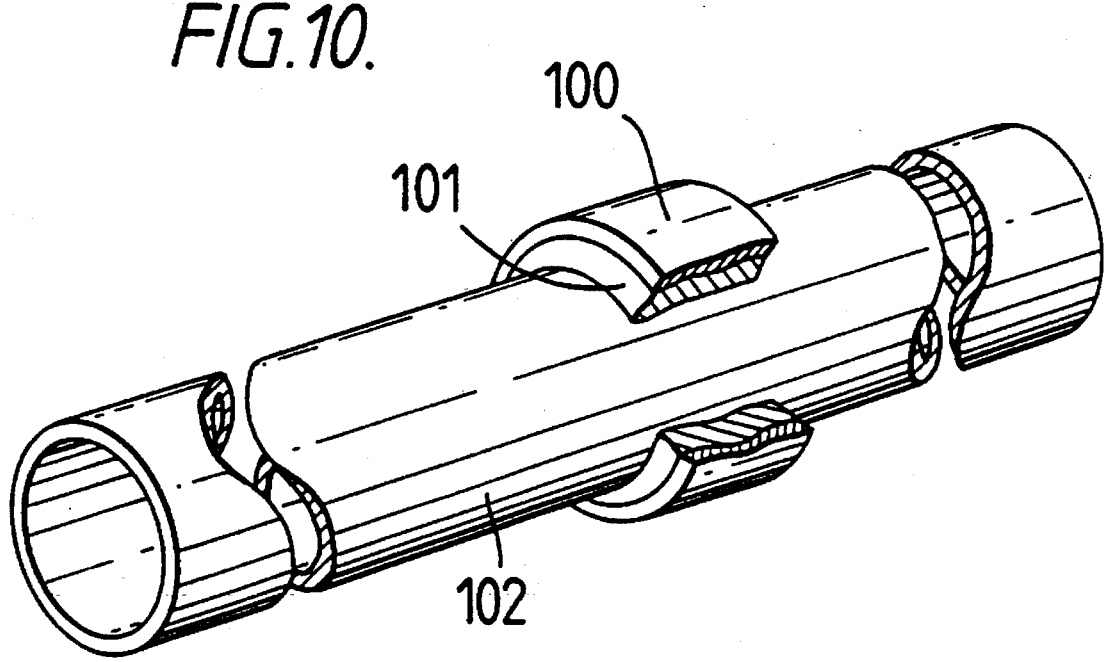

FIG. 9 illustrates a further modification of the arrangement shown in FIGS. 2 and 3. In the arrangement of FIG. 9, the piezo-electric annulus 10 has an axially extending flange 10a to which the electrical ribbon cables 13 are connected via the aforementioned metallised coating 14 of gold. With this arrangement, there is increased stability of the assembly compared with the arrangement shown in FIGS. 2 and 3 in which there is the epoxy bonding 16 between the proximal end of the piezo-electric annulus 10 and the pad 15 carrying the distal end of the ribbon cable 13.

FIGS. 10 TO 17

Figure 17:
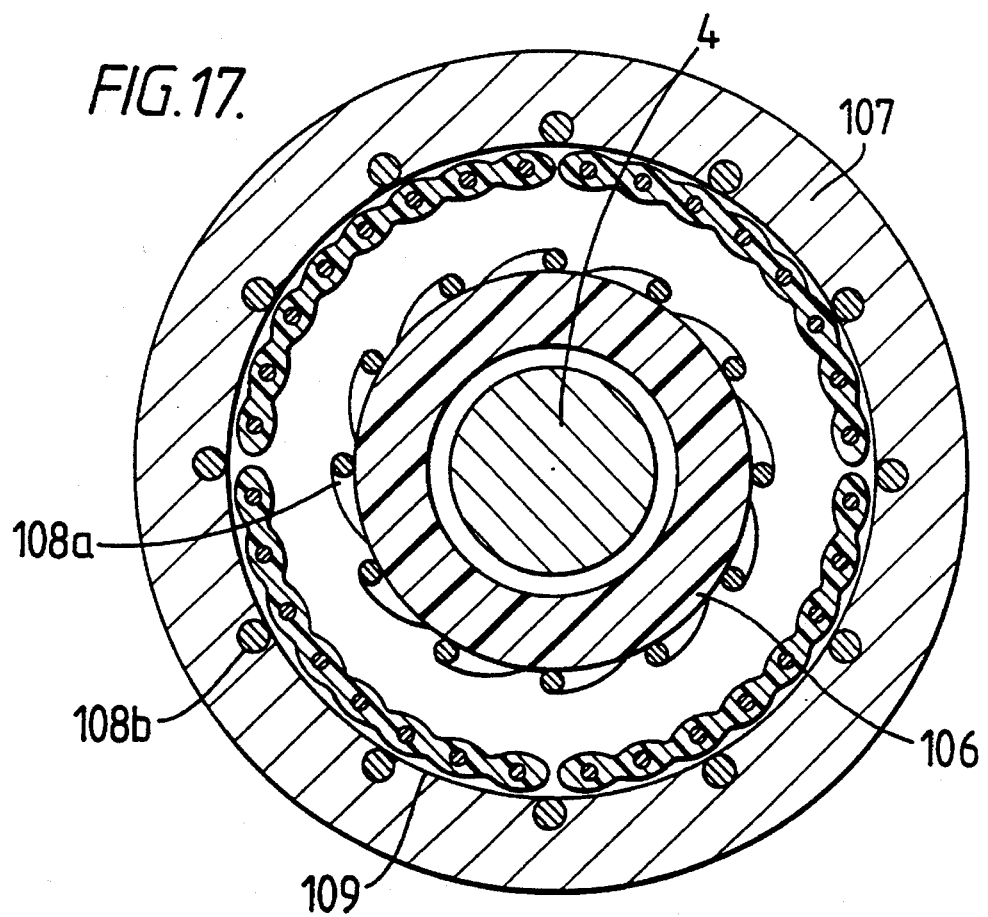
Figure 16:
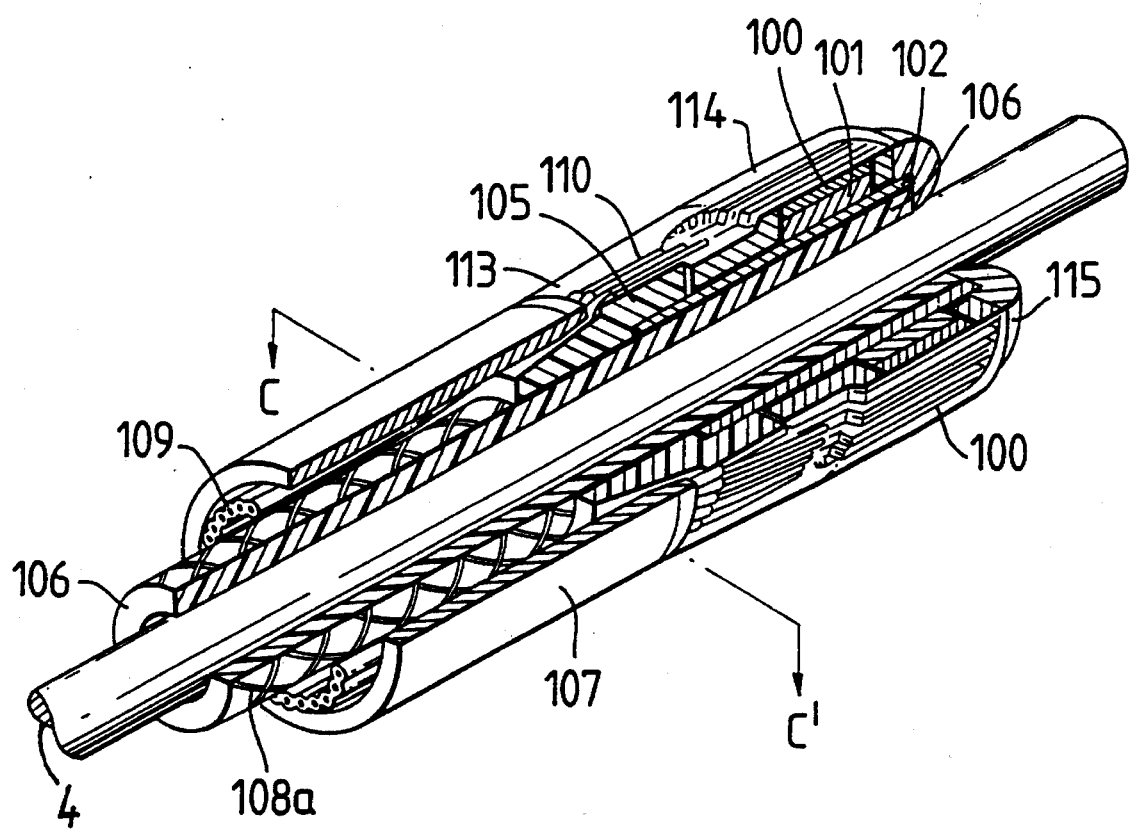

Referring firstly to FIGS. 15 to 17 which show the finished product.

The transducer arrangement comprises sixty-four transducer elements 100 made of PZT and arranged in an annular formation and supported on an acoustic backing layer 101 which in turn is carried by a metallised tungsten carbide tubular support or collar 102.

The transducer array 100 is sandwiched between two locating sleeves 103,104 also carried by the collar 102.

Adjacent the sleeve 104 is an annular wire retainer member 105 made by injection moulding from a biocompatible polymer such as ABS so that it has a certain amount of resilience. The member 105 is stepped at its internal diameter to form a first portion 105a which grips the end of the collar 102 and a second portion 105b of smaller internal diameter which grips the outside of the distal end of the inner body 106 of a catheter tube, the catheter having an outer body 107. The inner body 106 is made of a plastic material and has helical metal reinforcement 108 to give it the required tensile strength to enable it to be extracted from a patient after use.

The transducer array 100 is energised through and resulting echo signals transmitted back by means of four ribbon cables 109 each one of which consists of eight leads to give a total of thirty-two leads.

The distal end 110 of each lead is stripped of insulation and soldered at 111 to bond pad 112 formed on the stepped down (reduced diameter) portion of the rear sleeve 104.

The stripped ends of the wires are located in slots in the wire retainer 105 and gripped by the sides defining those slots.

The distal end of the outer body 107 of the catheter encloses and grips the insulated distal ends of the ribbon conductors 109. A sealing compound 113 encapsulates the bare ends of the conductors and together with the outside of the outer body 107 forms a continuous smooth external surface.

An acoustically transparent quarter-wave matching layer 114 encapsulates the transducer elements 100 to not only isolate them from the patient but to acoustically match the vibrating transducer elements to the body fluid of the patient, e.g blood.

The end of the transducer arrangement/assembly is provided with a rounded annular end cap 115 to give the distal end of the catheter a smooth rounded end in order to facilitate its insertion into the patient's artery.

It will be appreciated that given the very small size of the transducer arrangement and the very limited amount of space between the inner and outer bodies of the catheter there is a potential problem in being able to provide enough electrical leads to energise all the transducer elements and carry signals representative of the ultrasonic echoes.

The desired frequency of vibration of the transducer elements in the radially outer direction is 20 MHz in this embodiment. To achieve this the transducer annulus requires to be a particular thickness for a given material, in this case about 75 μm thick.

With this embodiment there are thirty-two electrical leads from the proximal to the distal end of the catheter to energise the transducer array and to transmit the echo signal. If the annulus 100 were to be divided into thirty-two segments, to match the number of leads, it would result in each segment being a relatively low depth to width ratio (referred to as the aspect-ratio) of roughly 80:120. As a result there would be a significant lateral or tangential ultrasonic signal at ninety degrees to the desired radial signal which lateral signal would interfere with the radial signal.

In order to eliminate this interference or at least reduce it to an acceptable level the depth of the discrete transducer elements needs to be significantly greater than their width.

To achieve this the present invention divides each of the thirty-two transducer elements into two and by this means provides each element with the required aspect ratio to ensure that any lateral signal is not significant. Depending upon the geometry and size of the transducer arrangement and the manufacturing technology available each element may be divided into a greater number than two to give the desired performance.

Each of the thirty-two leads energises a pair of transducer elements, typically 100a, 100b, through a single associated conducting bond pad 112a (FIG. 12), the elements 100a, 100b of a pair being separated by a slot 117 and the pair itself being separated from the two adjacent pairs by slots 116.

Both the slots 116 and the slots 117 extend the length of the cylindrical PZT transducer member 100 but the slots 116 in addition extend into the rear sleeve 104.

The portions of the slots 116 in the member 100 are 0.13 mm deep and 0.025 mm wide whereas the slots 117 are only 0.10 mm deep but the same width.

Figure 13:
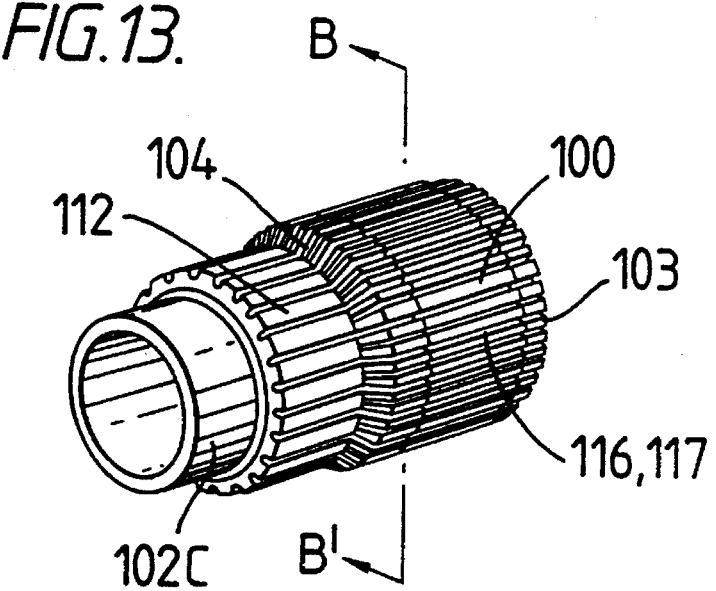
Figure 14:
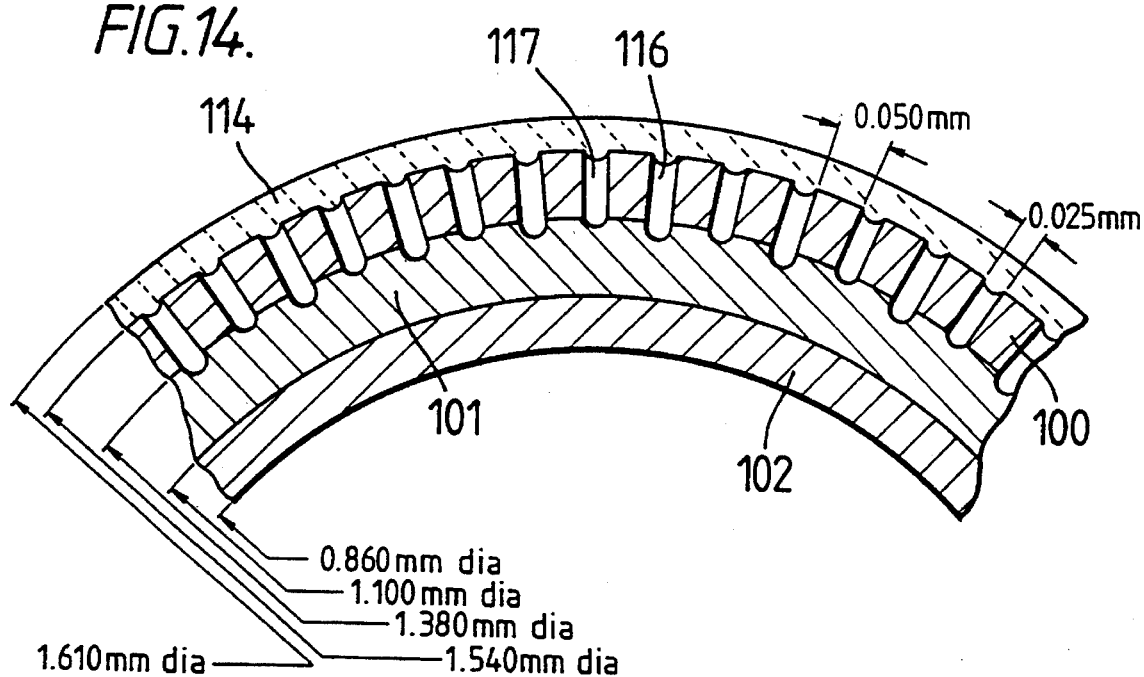

FIG. 14 is a cross-sectional view of a segment of the transducer arrangement taken on the line B–B' of FIG. 13.

The spacing between the two types of slot 116,117 is approximately 0.05 mm. The radial dimensions of the arrangement are shown in FIG. 14.

The various steps involved in the manufacture of the transducer arrangement will now be described with reference to FIGS. 10 to 17.

A metallised tungsten carbide collar or sleeve 102 is provided which has an accurately formed outer surface to act as a datum and an axial length substantially greater (FIG. 10) than the axial length of the finished product (FIG. 15), This is so that the ends of the collar or sleeve 102 can be gripped in precision collets or V-blocks in order to enable the collar to be accurately located and rotated during manufacture and the outer surface to act as a datum. An alternative (not illustrated) could be to accurately form the inner surface to act as a datum in which case the sleeve 102 need not be longer than its finished length.

The first manufacturing step is to secure a PZT ultrasonic transducer annulus 100 to the collar 102 by means of an acoustic backing layer 101 which is electrically conducting so that there is an electrical path from the annulus 100 through the layer 101 to the collar 102.

The metallised layers on the collar are put there by a sputtering method which will be described in more detail later.

The annulus 100 is mounted accurately coaxially with respect to the collar 102 by using a sacrificial jig the acoustic backing layer being injected into the annular space between the outside radial surface of the collar 102 and the inside radial surface of the annulus 100. At this stage the PZT annulus 100 has a greater thickness than is eventually required.

Figure 11:
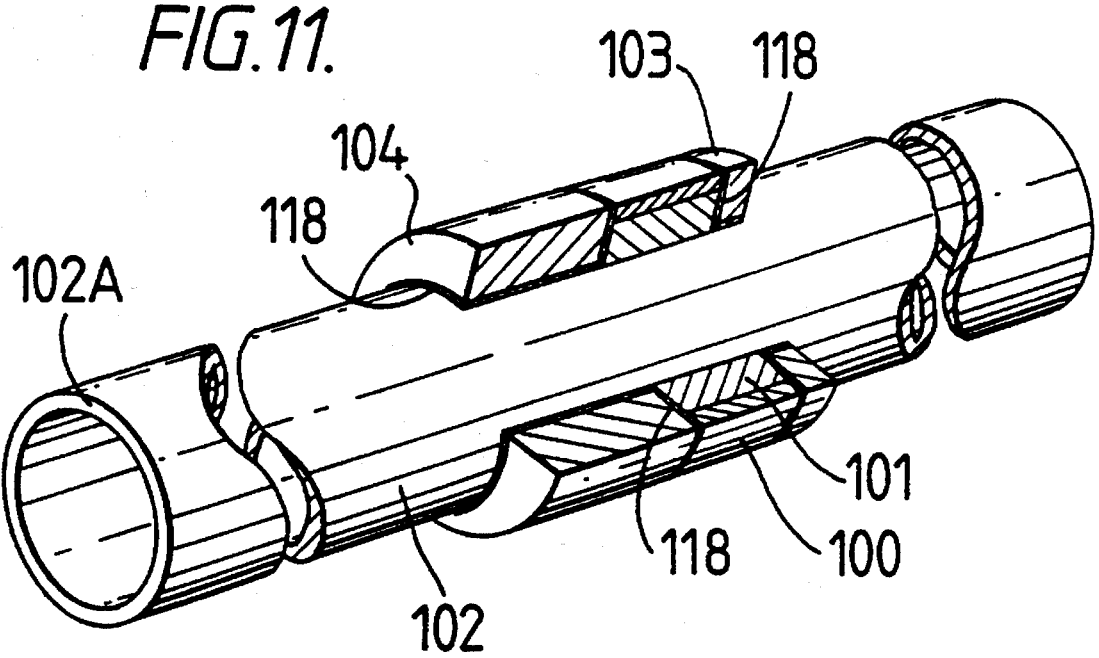

FIG. 11 shows the next step in the manufacturing process in which the two axially locating front and rear sleeves 103 and 104 respectively are located in position on the collar 102.

The sleeves 103 and 104 are secured to the collar 102 by non-conducting adhesive 118, the same adhesive also being between the axial/radial end faces of the annulus 100 and the sleeves 103 and 104 to stop the electrodes on the inner and outer surfaces of the PZT sleeve from shorting to each other.

Before the addition of the sleeves the end faces of 100 and 101 are machined square with respect to the collar 102. The annulus 100 and the sleeves 103,104 are then turned down using precision grinding wheels to the required external diameter by rotating the collar 102 by its ends 102A,102B in precision V-blocks to produce the diameters shown in FIGS. 12 to 14, i.e. from about 1 mm to about 0.8 mm for the annulus 100.

Figure 12:
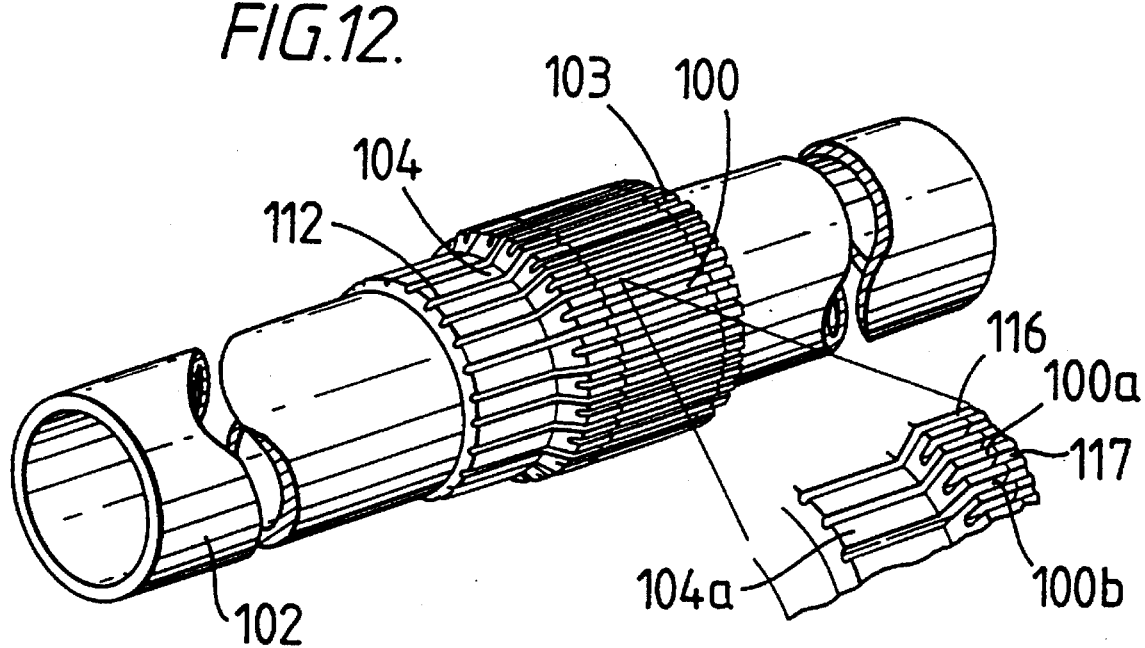

The next step is to form the slots 116,117 shown in FIG. 12. This is done by means of a diamond impregnated saw blade which is only 0.015 mm or 0.02 mm thick.

The ends 102A,102B are then machined off to leave the collar 102 the length shown in FIGS. 13 to 17.

The collar 102 has a protruding larger end 102C which has its outer diameter machined down to accommodate the relatively resilient plastic wire retainer collar 105. Alternatively with a thinner collar 102 no machining to reduce the diameter would be required.

FIG. 15 is a longitudinal section on the line B–B' of view of the completed transducer arrangement and also shows a protruding shorter end 102D to the collar 102.

The above gives a general description of the various steps involved in manufacturing the transducer arrangement shown in FIGS. 15 to 17. The following is a more detailed description of various aspects of the manufacturing process and the construction of the transducer arrangement.

Attachment of Interconnect Conductors to the Catheter Tip Array

The transducer array with electrical leads attached is first formed as a sub-assembly and then fitted to the catheter tubes in order to complete the catheter. The resilient wire retainer collar 105 is first snapped onto the extension 102C of the support collar 102.

Then it is necessary firstly to position the conductors 110 above their respective bond pads 112 and secondly by a wire-bonding process to bond the conductors 110 to the bond-pads 112. The former is achieved by means of the plastic moulded wire-retainer collar 105 which is attached as described earlier and accurately concentric with the bond-pad array. The latter is achieved by means of micro-soldering.

The wire-retainer collar 105 consists of thirty-two slots at a pitch and height suitable to guide each conductor 110 to a position centrally above each bond-pad 112. The direct attachment of the wire-retainer 105 to an extension of the tungsten carbide support cylinder 102 ensures that the wire-retainer 105 and bond-pad array 112 are held rigidly adjacent one another. The wire-retainer 105 supports the flying conductor leads by means of adhesive and, in addition to providing location for the conductors, will also act as a stress relief point for the wire connection 110 to the bond-pad 112. Wire-bonding involves the selection of appropriate materials for (i) the bond-pad substrate 104, (ii) the bond-pad metallisation, (iii) the conductor 110 and (iv) the conductor plating.

The substrate 104 is required to possess suitable properties, both mechanical and electrical. In respect of mechanical properties, the substrate 104 must be capable of being ground to a good surface finish and of being slotted at approximately 0.1 mm intervals by a diamond impregnated saw blade only 0.015 mm thick.

Furthermore, the land between the slots must be capable of supporting the force applied by a wire-bonding tool. In respect of electrical properties, the substrate 104 must be a good insulator with low dielectric loss, and be capable of supporting with good adhesion a metallisation layer less than 0.002 mm thick deposited by vacuum techniques.

Some well-known engineering ceramics are excluded on the grounds that they are suitable electrically but not mechanically, and vice versa. Thus, for example, alumina shows good ahesion to several types of sputtered or evaporated metallisation, but is extremely difficult to slot. "Macor" responds well to grinding and slotting, but the adhesion of metallised layers is poor and the ceramic land between the slots does not adequately support the wire-bonding stress. A machineable grade of aluminium nitride (with boron nitride as the main additive) has been found (i) to give slots of excellent quality, (ii) to possess adequate compressive strength and (iii) to be capable of being metallised with sputtered copper (and associated seed and antioxidation layers) with good adhesion. The machineable aluminium nitride is known by the trade-name Shapal-M.

Various metallised layers less than 0.002 mm thick can be deposited by sputtering. The choice of TiW—Cu—Au (titanium-tungsten, copper, gold) metallisation provides (i) the optimum adhesion to the aluminium nitride substrate and (ii) a tried and tested system for tin-lead solder reflow on to a copper base layer (see below). In the TiW—Cu—Au system, the approximate layer thicknesses are:

| TiW | 0.0001 mm |
| Cu | 0.0018 mm |
| Au | 0.0001 mm |

The TiW "seed layer" provides excellent adhesion to both Shapal-M and PZT components, the Au antioxidation layer provides surface corrosion protection, and the Cu is the main conducting layer to which the reflow-soldered bond is made (the thin gold layer being absorbed into the solder). The electrode adhesion is critical in this application because of the small dimension of the bond pad 112 (approximately 0.1 by 0.2 mm).

The choice of alloy for the 0.04 mm diameter interconnect conductors 110 is based on considerations of (i) electrical resistivity, (ii) tensile strength and (iii) ductility. A low electrical resistance (e.g pure copper) is associated with an inadequately low tensile strength, and conversely a high tensile strength (e.g copper-beryllium alloy) is associated with high electrical resistance and insufficient ductility. A copper-tin alloy has been found to provide adequate conductivity, tensile strength and ductility, and has the added advantage that its physical properties can be tailored by pre-annealing.

A tin-lead solder layer 0.003 mm thick is deposited on the stripped end sections of the interconnect conductors 110 by electroplating. The wire-bonding process consists of reflow of the tin-lead solder onto the Cu component of the TiW—Cu—Au metallisation, the tin-lead to copper bond being a well understood technology.

The wire-bonding process selected is known as "parallel-gap resistance reflow" and is well-established, with larger conductors and bond-pads, in particular with flat geometry devices. However, the small size of the ultrasound catheter and the three-dimensional geometry of the tip array both combine to make the bonding process a problem.

The main technical problems relate to (i) the small size of the bond-pads 112 (0.10 by 0.2 mm), (ii) the "flying" nature of interconnect conductors 110 (wire-bonding is normally between adjacent pads on a flat substrate), (iii) the cylindrical configuration of the bond pad array 112 and (iv) the compatibility of the substrate material, metallisation layer and reflow process. The tin-lead electroplated layer on the conductors 110 reflows to form a reliable soldered bond to the Tiw—Cu—Au metallised Shapal-M substrate. It has been found that reflow "brazing" of this kind is more suitable than pure resistance welding.

The interconnect cable conductors 110 are coated with an insulating dielectric of low loss and low permittivity. As described in one embodiment the conductors are grouped together in an insulating web to form a "ribbon cable" with eight conductors, although there could be more. The spacing between the conductors 110 is selected (i) to match the pitch of the slots in the wire retainer 105, (ii) to match the space available between inner and outer catheter bodies 106,107 and (iii) to reduce the electrical cross-talk between adjacent conductors. In a second embodiment the conductors are insulated individually and wound helically onto a metallic screen on the inner catheter body 106. In both embodiments the insulated conductors are metallised on the outer surface of the insulation by a vacuum sputtering process. This external metallisation reduces rf interference and transforms the interconnect cable into a well-characterised "transmission line". In the case of the helical winding the pitch can be selected to determine the length and therefore the properties of the transmission line. The metallic screen on the inner catheter body (an electroless metallic coating or winding or both) serves, in addition, to reduce the electrical resistance of the sputtered metallic layer on the interconnect cables; that is there is a physical contact between the sputtered layer and the more conducting environment on the inner body.

We claim:

1. A method of manufacturing a transducer array which comprises the steps of:

a) mounting an annular electrically conducting transducer member on a support sleeve by means of an acoustic backing layer;

b) mounting two locating sleeves on the support sleeve, one adjacent each of the two ends of the annular transducer member respectively;

c) machining the outer surface of the annular transducer member and sleeves to the desired profile; and d) sawing longitudinally extending slots in the annular transducer member to define a plurality of discrete transducer elements.

2. A method as claimed in claim 2 including the step of forming a plurality of bond pads on one of the locating sleeves and connecting an electrical lead to each bond pad to enable an associated transducer element or elements to be electrically energized.

3. A method as claimed in claim 2 in which each electrical lead is first spaced radially outwardly from its associated bond pad and an electrical and physical connection is then made by filling the gap between the lead and the bond pad with an appropriate material.

4. An ultrasonic transducer array comprising an annulus of piezo-electric material having a plurality of physical discontinuities defining a plurality of transducer elements separated from each other, a metal support, said annulus being relatively rigid and being mounted on said support, and a relatively flexible acoustic backing layer between said annulus and said support.

5. An array as claimed in claim 4 in which said acoustic backing layer comprises a silver loaded epoxy resin.

6. An array as claimed in claim 4 in which said annulus is made of a polarized lead zirconate titantie (PZT) and said transducer elements are defined by circumferentially spaced grooves in said annulus and which run substantially parallel to the axis of said annulus.

7. An array as claimed in claim 4 in which said piezo-electric material is PZT and said support is a tungsten carbide tube, said annulus is bonded to said tube.

8. An array as claimed in claim 4 in which said annulus has a pair of ends and at least one of said ends is supported by a rigid ring bonded to said support to increase the stability of the assembly.

9. An array as claimed in claim 4 which has an outer diameter no greater than 2 mm and the number of said transducer elements is at least 32.

10. An array as claimed in claim 4 in which said annulus has an axially extending portion flange for supporting electrical contact points for the electrical energization of the transducer array and for the return of echo signals from the transducer array.

11. An array as claimed in claim 4 including electrical connections to the piezo-electric transducer array, each said connection includes a metallized layer formed on the piezo-electric material by sputtering.

12. An array as claimed in claim 4 including electrically conducting tracks on a flexible support mounted on said annulus.

13. An array as claimed in claim 4 in which said annulus has an outer face that is both acoustically matching and biocompatible.

14. An array as claimed in claim 4 in which said annulus has an axially extending portion of smaller external diameter than the external diameter of the annulus and which smaller diameter portion is divided into separate axially extending bond pads to which electrical conductors are secured for the electrical energization of said transducer elements and the return of echo signals from the transducer elements.

15. An array as claimed in claim 14 including electrical conductors which are bonded to said bond pads.

16. An array as claimed in claim 15 in which the ends of said conductors are spaced radially outwardly from said transducer array leaving a gap between the array and the conductors, said gap being filled with a re-flow material.

17. An array as claimed in claim 14 including electrical supply cables in the form of ribbon cables.

18. An array as claimed in claim 14 including electrical conductors for energizing the transducer array, said conductors being helically wound.

19. An array as claimed in claim 14 including a resilient sleeve having axially extending slots through which electrical conductors pass and are gripped thereby.

20. An array as claimed in claim 4 in which said annulus is joined to said support by a diffusion process.

21. An array as set forth in claim 4 in which said annulus is joined to said support by a glass interlayer process.

22. An array as claimed in claim 4 including at least one ribbon cable for energizing said array, said cable being externally metallized to reduce radio frequency interference and electrical cross-talk.

23. An array as claimed in claim 4 in which the distal end of the transducer array is provided with a rounded plastic end cap.

24. The combination of the transducer array as claimed in claim 4 with a catheter, the transducer array being mounted on the distal end of the catheter.

25. A method of manufacturing an ultrasonic array which comprises the steps of:
   (a) mounting an annular electrically conducting transducer member on a metal support sleeve by means of an acoustic backing layer; and
   (b) mounting two locating sleeves on the support sleeve one adjacent each of the two ends of the annular transducer member respectively in order to increase the stability of the resulting assembly.

26. A method as claimed in claim 25 comprises the further steps of:
   (a) machining the outer surface of the annular transducer member and sleeves; and
   (b) sawing longitudinally extending slots in the annular transducer member to define a plurality of discrete transducer elements.

27. A method as claimed in claim 26 including the step of forming a plurality of bond pads on one of the locating sleeves and connecting an electrical lead to each bond pad to enable an associated transducer element to be electrically energized.

28. A method as claimed in claim 27 in which said electrical lead is first spaced radially outwardly from its associated bond pad and an electrical and physical connection is then made by filling the gap between the lead and the bond pad with a re-flow material.

* * * * *